United States Patent [19]

Geary

[11] Patent Number: 5,167,947
[45] Date of Patent: Dec. 1, 1992

[54] ENHANCEMENT OF ABSORPTION OF RADIOPROTECTIVE DRUGS

[75] Inventor: Richard Geary, San Antonio, Tex.

[73] Assignee: Southwest Research Institute, San Antonio, Tex.

[21] Appl. No.: 428,150

[22] Filed: Oct. 26, 1989

[51] Int. Cl.⁵ .................. A61K 49/00; A61K 31/43
[52] U.S. Cl. .................................. 424/11; 514/109; 514/562
[58] Field of Search ............... 424/1.1; 514/109, 562

[56] References Cited

U.S. PATENT DOCUMENTS

| | | |
|---|---|---|
| 4,537,772 | 8/1985 | Alexander et al. |
| 4,713,246 | 12/1987 | Begum et al. |
| 4,729,989 | 3/1988 | Alexander et al. |
| 4,764,380 | 8/1988 | Urquhart et al. |
| 4,822,773 | 4/1989 | Alexander et al. |

FOREIGN PATENT DOCUMENTS 1165689  4/1984  Canada.

OTHER PUBLICATIONS

Suzuka, et al, Effect of Salicylate and Disodium Ethylenediaminetetraacetic acid on the rat intestinal absorption of defmetazole (1985) Chem. Pharm Bull. 33:4600–4605.

Yamashita et al, Characterization of Enhanced Intestinal Permeability and the Electrophysiological Study on the Effects of Diclofenac and Ethylene-diaminetetraacetic acid, (1985), J. Pharm. Pharmacol 37:512–513.

Fleckenstein et al, Bioavailability and Newer Methods of Delivery of Phosphorothioate Radioprotectors, (1988) Pharmac. Ther. 39: 203–212.

Primary Examiner—Robert L. Stoll
Assistant Examiner—C. Sayala
Attorney, Agent, or Firm—Fulbright & Jaworski

[57] ABSTRACT

The present invention provides a pharmaceutical composition for enhancing gastrointestinal tract absorption of a radioprotective drug comprising a therapeutically effective dosage amount of a bioactive polar radioprotective agent, such as ethiofos, its active metabolites, and pharmaceutically acceptable salts thereof and a chelating agent selected from the group consisting of EDTA, EGTA, citrate and therapeutically acceptable salts thereof.

A method for enhancing the rate of gastrointestinal absorption of radioprotective agents is also provided.

10 Claims, 6 Drawing Sheets

ENHANCEMENT OF ABSORPTION OF RADIOPROTECTIVE DRUGS

This invention was made under United States Government Contract No. DAMD17-86-C-6153 (USAMRDC) and the United States Government has a nonexclusive, nontransferable, irrevocable, paid-up license to practice or have practiced for or on behalf of the United States, this invention throughout the world.

BACKGROUND OF THE INVENTION

The invention relates to novel compositions and methods for enhancing absorption of radioprotective drugs from the gastrointestinal tract by incorporating therein ethylenediaminetetraacetic acid as an absorption enhancing agent.

DESCRIPTION OF THE PRIOR ART

Though the gastrointestinal tract is the preferred route for drug delivery, all drugs are not well absorbed from this site. In many cases, this may be due to the polar nature or hydrophilic character of the drugs. Since they are precluded from rapid absorption, such drugs are subject to long residency time in the gastrointestinal environment, where both acidic and enzymatic degradation contribute to their poor bioavailability. It is, therefore, clear that any factor which enhances the rate of absorption will demonstrate improved clinical efficacy. In recent years, considerable effort has been directed toward identifying agents which increase gastointestinal absorption of poorly absorbed drugs. For example, surface active agents (George, Sutter, Finegold, J. Infect. Dis. 136, 822 (1977)), chelating agents (Cassidy, Tidball, J. Cell Biol. 32,672 (1967)), salicylates (Higuchi, et al., U.S. Pat. No. 4,462,991 (1984)), antiinflammatory agents (Yaginuma et al., Chem. Pharm. Bull. 29,1974 (1981)) and phenothiazines (Alexander and Fix, U.S. Pat. No. 4,425,337 (1984)) have been shown to increase gastointestinal permeability of several drugs.

There is an important need for the development of an orally-administered radioprotective drug. An oral therapeutic agent, administered chronically for the protection of critical body tissues against low to moderate doses of ionizing radiation, might protect human populations from the radiation hazards of nuclear events. The recent Chernobyl accident is an example of such an event; nuclear material was distributed over a wide area, and contaminated vast, populated areas with radiation. Such a radioprotective agent would be potentially useful to both emergency personnel and civilian populations during disaster operations and, one would hope, exert beneficial antimutagenic and anticarcinogenic effects on populations living in areas with long-term, low-level radiation exposure.

Although many compounds have radioprotective activity, the most promising radioprotective drugs are aminoalkylaminoethane phosphorothioates (Sweeney, A Survey of Compounds from the Antiradiation Drug Development Program of the U.S. Army Medical Research and Development Command; Walter Reed Army Institute of Research, Washington, D.C. 1979). When administered intravenously, the best phosphorothioate compound, S-2-(3-aminopropylamino)ethylphosphorothioic acid (ethiofos, WR-2721), has been shown to protect mice, dogs, and Rhesus monkeys against X-rays and gamma radiation. Oral dosing of ethiofos, however, failed to protect either dogs or monkeys, suggesting poor bioavailability of the drug (Davidson et al., Biological characteristics of some improved radioprotectors in: Radiation Sensitizers: Their Use in the Clinical Management of Cancer, pp. 309-320, Brady, L.W. (ed.), Masson, N.Y. 1980)). Further evidence of incomplete bioavailability was seen in a comparison of approximate $LD_{50}$ values following intraperitoneal (950 mg/kg) and oral (1500 mg/kg) administration in mice (Sweeney, 1979).

The absorption of the radioprotector ethiofos (WR-2721) has proved to be unusually limited because its bioavailability is compromised by several factors. The low bioavailability of the orally-administered drug is due not only to incomplete alimentary absorption, but also to first-pass metabolism during absorption. The first-pass metabolism appears to occur at both the gut wall and the liver. Ethiofos can be hydrolyzed in the acidic environment of the stomach, and the drug can slow stomach motility and gastric emptying. By slowing the delivery of the drug to the optimum site for absorption there is probably a more complete removal of the drug by first-pass metabolism. In addition, the small intestine may be a site of further drug metabolism via the alkaline phosphatase enzymes found in the brush border (Stewart, J. Pharm. Sci. 75(10), 940-945 (1986); Mori, et al., J. Radiat. Biol. 10, 1529-1531 (1985).

Ethiofos is metabolically converted to form an active radioprotective species, WR-1065 (Puride et al., Int. J. Radiat. Biol. 43:517-527 (1983)) by dephosphorylation as a result of enzymatic hydrolysis by alkaline phosphatase (Mori, et al., Int. J Radiat. Oncol. Biol. Phys. 10:1529-1531 (1984)). The thiol can undergo disulfide formation with itself to form the symmetrical disulfide (WR-33,278) or form disulfides with nonprotein thiols or with proteins. Disulfide formation is a reversible reaction.

Ethiofos has also been proposed as a treatment agent for pathological conditions such as hypercalcemia and prevention of cancer.

When ethiofos is administered intravenously to rhesus monkeys at a dose of 150 mg/kg, 80% of the ethiofos or its metabolites is excreted in the urine within 120 hours, with most of the drug (or its metabolites) being excreted within 24 hours. Ethiofos itself has a plasma halflife of only approximately 18 minutes. WR-1065, the dephosphorylated metabolite, is the bioactive metabolite and has a much long halflife. (Fleckenstein et al., J. Pharmac. Ther. 39:203-212 (1988)). However, the free thiol is much more toxic to the individual than the parent drug, ethiofos. Radioprotective plasma levels can not be achieved by iv administration of the free thiol without causing acute toxicity. Thus, administration of the parent compound, ethiofos, decreases the toxicity of the free thiol, enhances effective distribution of the radioprotective drug to tissues thereby producing better radioprotection to the individual.

Formulation approaches to bioavailability problems such as enteric coating or microencapsulation can protect the drug from acid degradation and possible overcome problems of delayed stomach emptying. However, it is also likely that the polar nature of ethiofos limits its ability to cross lipoidal membrane barriers found in the stomach and small intestine.

Thus, in order to provide an effective radioprotective treatment which can be easily administered, especially in emergency situations, it was desirable to provide an oral composition of the radioprotective drug which would be capable of gastric absorbtion and provision of effective radioprotecting plasma levels of the radioprotective drug.

SUMMARY OF THE INVENTION

It has been found that when ethiofos $NH_2CH_2CH_2CH_2NHCH_2CH_2SPO_3H_2 \cdot 3H_2O$ (WR-2721) and its active metabolites, particularly $NH_2CH_2CH_2CH_2NHCH_2CH_2SH$ (WR-1065), are administered orally or rectally, the bioavailability of these drugs are increased by incorporating therein a salt of a chelating agent selected from the group consisting of EDTA, EGTA, citrate and therapeutically acceptable salts thereof, preferably a salt of ethylenediaminetetraacetic acid (EDTA) as an absorption enhancing agent.

It is a further object of this invention to provide a new dosage form utilizing EDTA and salts thereof which, when administered orally or rectally with ethiofos or its active metabolites, will provide an increased blood level of ethiofos and/or its active metabolites.

It is a further object of the invention to provide dosage formulation of ethiofos and/or its active metabolites which, when administered orally or rectally, provides a bioavailable radioprotective drug.

It was a further object of the invention to provide a dosage form of ethiofos and/or its active metabolites which provides a bioavailable drug for the treatment of hypercalcemia and the prevention of cancer.

Other objects, features and advantages of the invention will be apparent to those skilled in the art from the detailed description of the invention which follows.

All of the foregoing objects are readily attained by providing a composition and method wherein oral and rectal absorption of ethiofos and its active metabolites is enhanced. The method comprises the steps of preparing a dosage form suitable for oral or rectal delivery, and a dosage form comprising an effective unit dosage amount of a poorly absorbed radioprotective agent such as ethiofos and/or its active metabolites EDTA or pharmaceutically acceptable salts thereof, the EDTA being present in said dosage form in an amount sufficient to be effective in enhancing the rate of the oral and rectal absorption of the radioprotective agent, and pharmaceutically acceptable excipients.

DETAILED DESCRIPTION OF THE DRAWINGS

FIG. 2 demonstrates the increase in plasma concentration of ethiofos as a function of EDTA concentration.

Specifically.

DETAILED DESCRIPTION OF THE INVENTION

The present invention is directed to a method of enhancing the rate of gastrointestinal absorption of an orally or rectally administered radioprotective agent. The method generally comprises administering a dosage form capable of being orally or rectally administered, wherein the dosage form comprises a therapeutically effective dosage amount of a poorly absorbed radioprotective agent and EDTA a chelating agent selected from the group consisting of EDTA, EGTA, citrate and therapeutically acceptable salts thereof, preferably, or its pharmaceutically acceptable salts as an absorption enhancing agent, the EDTA being present in the dosage form in a sufficient quantity to be effective in enhancing oral and rectal absorption rates.

The combination of ethiofos and the described absorption enhancer(s) may be useful for radioprotection, the treatment of hypercalcemia, and potentially, for prevention of cancer. The mechanism of radioprotection may involve the ability of the free thiol to scavenge free radicals induced by radiation or by decreasing the oxygen content of the blood and blood perfused tissues thus reducing the production of free radicals. Free oxygen radicals are suspected in radiation induced tissue damage. This mechanism of action (free radical scavenging) suggests that ethiofos will also be useful in preventions of cancer induced by DNA damage caused by free radicals.

Blood chemistries taken during ethiofos treatment in human clinical trials indicated a loss of circulating calcium. Ethiofos has been postulated as a treatment for hypercalcemia.

The compounds that are used as radioprotective drug absorption enhancers in the present invention are EDTA and its pharmaceutically acceptable salts, as well as other chelating agents such as EGTA and its pharmaceutically acceptable salts. Most preferably, the disodium salt of EDTA is used to enhance the absorption of the radioprotective drugs.

The drugs absorption enhancing agents employed in the practice of this invention are known compounds which are commercially available, and processes for their preparation are disclosed throughout the art.

The radioprotective drugs are not readily bioavailable when administered orally or rectally which can be made more useful by enhancing their absorption in accordance with this invention are exemplified by, but are not limited to, ethiofos and its active metabolites such as WR-1065.

The amount of poorly absorbed drug varies over a wide range. However, the therapeutically effective unit dosage amount of the selected poorly absorbed radioprotective drug depends on that amount known in the art to obtain the desired results.

Generally, the amount of EDTA enhancer employed in the practice of the invention ranges from about 5 to about 95 mg in each unit dose, preferably EDTA ranges from 25-80 mg in each unit dose. The percentage of EDTA in the total combination of drug plus enhancer being 5-15% w/w, with a preferred ratio of EDTA in the total combination of EDTA plus drug being 10-15%, the remaining percent being the drug and, optionally, other excipients.

For oral administration, the formulations may be prepared as liquids, suspensions, capsules, tablets, coated tablets, and other standard procedures known in the art. A preferred formulation is a part geletin capsule composed of 500 mg ethiofus and 50 mg of EDTA and sufficient excipients to formulate an acceptable composition. Most preferably, the capsule comprises (a) microencapsulated EDTA and (b) enterically coated microencapsulated EDTA, and ethiofos. For rectal application, the formulations may be prepared as microenemas, suppositories, rectal tablets, and other standard procedures known in the art. A preferred formulation is a solid suppository composed of a minimum of 25 mg EDTA with the pharmacologically required dose of ethiofos preferably 150 mg/kg, and sufficient suppository base to formulate an acceptable composition. The methods and choice of excipients and suppository bases are well known to those skilled in the art, and the compositions of said formulations are not limited to gelatin capsules, compressed tablets or solid suppositories by this invention.

A most preferred formulation comprises a capsule which contains EDTA encapsulated in a trigyceride matrix which would be immediately released upon ingestion together with enteric coated microspheres containing both ethiofos and EDTA. Alternatively, EDTA and ethiofos may be encapsulated in the same enterically coated microspheres and a preloading dose of EDTA alone may be administered prior to administration of the combined dosage of ethiofos and EDTA.

In one embodiment, the oral dosage form provides microspheres containing EDTA together with microspheres containing EDTA and ethiofos encapsulated together.

Alternatively, the EDTA and enterically coated or non-coated ethiofos could be administered in separate oral dosage forms sequentially.

The method of encapsulating drugs is known in the art. For instance, one could utilize the method disclosed in U.S. Pat. application Ser. No. 07/320,500.

Most preferably, the ethiofos dosage form of the present invention will be coated so as to retard dissolution prior to reaching the stomach.

The following examples illustrate the effectiveness of the compositions of the present invention in enhancing the bioavailability of radioprotective drugs. The examples should be construed as illustrations rather than limitations hereof.

EXAMPLE I

Animal Models

An in situ rat and rhesus monkey models were used to demonstrate the enhancement of the bioavailability of ethiofos and its active metabolite WR-1065.

A. Rat Model

Male Sprague-Dawley rats were maintained on a regular diet of rat chow prior to dosing and fasted 16 h before the experiment. Water was available ad libitum.

Rats weighing between 250 g and 325 g were chosen and anesthetized with 50.0 mg/kg sodium pentobarbital ip. The cannulation of the intestine was performed as previously described. (Shanker, Tocco, Brodie and Hogben: J. Pharmacol Exp. Ther.; 123, 81–88 (1958)); (Doluisio, Billups, Dittert, Sugita, and Swintosky: J. Pharm. Sci.; 58, 1196–1200 (1969)).

The proximal cannula was inserted through the stomach wall past the pyloric sphincter for experiments which included the bile flow. Experiments which excluded the bile flow were cannulated approximately 3 cm distal to the pyloric spinchter. Five microcuries of ($^3$H)PEG 4000 was included in the perfusate to monitor water flux. For some experiments, 1 mCi of ($^{14}$C)ethiofos was added to the reservoir.

B. Monkey Model

An ethiofos solution was administered via rapid infusion through an infant nasogastric tube instilled in the duodenum of Rhesus monkeys. X-rays were taken to ensure proper location of the tube prior to drug administration. A dose of 150 mg/kg ethiofos (anhydrous) was dissolved in 5 ml of water containing an equimolar ratio of EDTA to ethiofos as that administered in the rat in situ experiment (1 mM EDTA: 47 mM ethiofos) and filtered. Prior to administration of dosing solution, 10 ml of 1 mM EDTA was predosed into the duodenum over 1 hr using a calibrated infusion pump.

C. Blood Sampling

Concommitant sampling of blood was accomplished by insertion of a catheter in the portal vein via the ileocecal vein. Blood samples were taken prior to dosing and 35, 65 and 95 min after initiation of drug perfusion. Samples of the circulating perfusate were taken from the reservoir at 0, 15, 30, 45, 60, 75 and 90 min. the perfusate reservoir was maintained at 37.5°±0.5° C. throughout the experiment and was stirred at all times using a magnetic stirrer. Rectal temperature was monitored in early experiments to assure maintenance of body temperature in this system.

EXAMPLE 2

Drug Assay in Blood and Intestinal Perfusate

An LDC Constametric III dual piston pump connected to a Waters Associates Model 712 refrigerated autosampler (WISP Model 712), and a Bioanalytical Systems MD-4000 pulse dampener was utilized to assay the plasma levels of the drug. Ethiofos was separated on a Bioanalytical Systems 5 mm Phase II $C_{18}$ ODS analytical column with an Uptight guard column packed with Whatman Pellicular $C_{18}$ 37-53 mm material. Amperometric detection was conducted with a Bioanalytical Systems LC 4B amperometric detector with a Hg/Au transducer ell. Detector signal was output to a Waters Associates Model 840 data system.

A 100-ml portion of blood was immediately treated with 200 ml of chilled (0°–4° C.) 1.0M HC10 containing 1 g/L EDTA. The samples were vortexed and centrifuged at 15,600×g for 45 sec. A 100-ml portion of the supernatant was added to 100 ml of prechilled solution containing 10 mg/ml of the internal standard, WR-80855. Samples were immediately frozen at −78° C. in a dry ice/2-propanol bath and transferred to a freezer maintained at −78° C.

The samples were prepared for HPLC analysis by adding 200 ml of buffer (pH 10). Samples were injected onto HPLC Unit A and amperometrically detected with an Hg/Au electrode at +0.25 V. The assay method has been previously described by Swynnerton, McGovern, Nino and Mangold: J. Radiat. Oncol. Biol. Phys.; 10, 1521-1524 (1984).

EXAMPLE 3

Quantitation of WR-1065 in Blood

Blood samples were analyzed for total material convertible to WR-1065 (total WR-1065). Aliquots of blood (100 ml) were treated as in the ethiofos assay to precipitate protein and 100 ml of the resulting supernatant was added to 100 ml of chilled (0°–4° C.) 0.5M chloroacetic acid/1.0M HClO$_4$ (3:1) buffer (pH 3.0) containing 1.0 mg/mL WR-1729 internal standard, mixed and frozen at −78° C. until workup. The analysis of total WR-1065 was achieved by reductive cleavage of disulfide conjugates and hydrolysis of ethiofos as described by Swynnerton, Huelle, Mangold and Ludden: Int. J. Radiat. Oncol. Biol. Phys.; 12, 1495–1499 (1986). Samples were injected on HPLC Unit B and amperometrically detected at +0.15 V.

EXAMPLE 4

Bioavailability of Ethiofos

Figure 1:
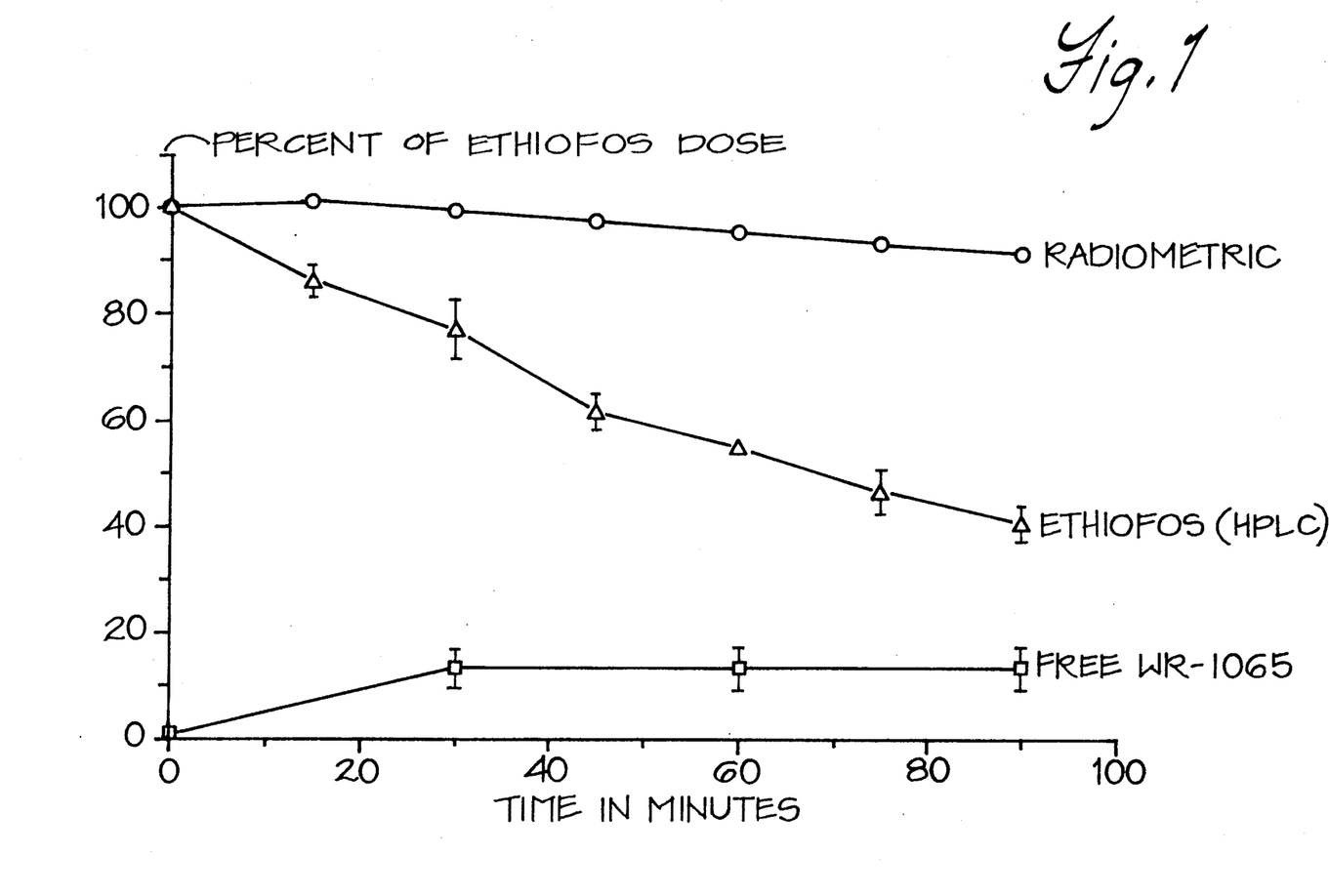
FIG. 1 shows the profile for radioactivity, ethiofos, and WR-1065 concentrations as a function of time in the rat.

FIG. 1 illustrates a complete profile for radioactivity, ethiofos, and WR-1065 concentrations as a function of time in the rat intestinal lumen during perfusion of [$^{14}$C]ethiofos in ph-adjusted water. Although the parent compound disappeared from the perfusate at a fairly rapid rate during the first 30 minutes of perfusion, the radiolabeled species did not appear to be absorbed until after the first 30 minutes. Furthermore, the free thiol (liberated by desphosphorylation of ethiofos) may promote absorption or be the primary absorbing species. Portal blood analysis for ethiofos and WR-1065 showed that transient and low levels of intact ethiofos were observed in blood while comparatively high levels of total WR-1065 were measured. Mass balance analysis of the perfusate data indicate that the ethiofos and measured metabolite account for approximately 85% of the radioactivity and provide evidence that the free thiol (WR-1065) is the major metabolite formed in the intestinal lumen. The 15% not accounted for by WR-1065 and ethiofos may be due to binding of WR-1065 to form symmetrical or mixed disulfides in the lumen of the rat small intestine.

EXAMPLE 5

Enhancement of Bioavailability of Ethiofos

Figure 2A:
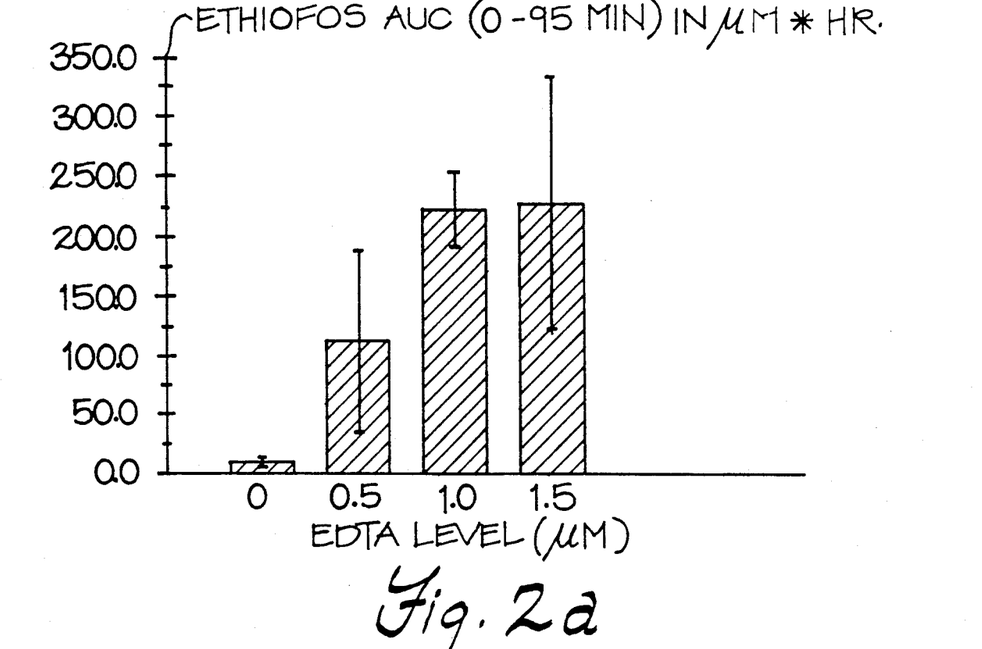
FIGS. 2a and 2b show a decrease in perfusate ethiofos was accompanied by a significant increase in plasma concentration of both ethiofos and its metabolite WR-1065, respectively.
Figure 2B:
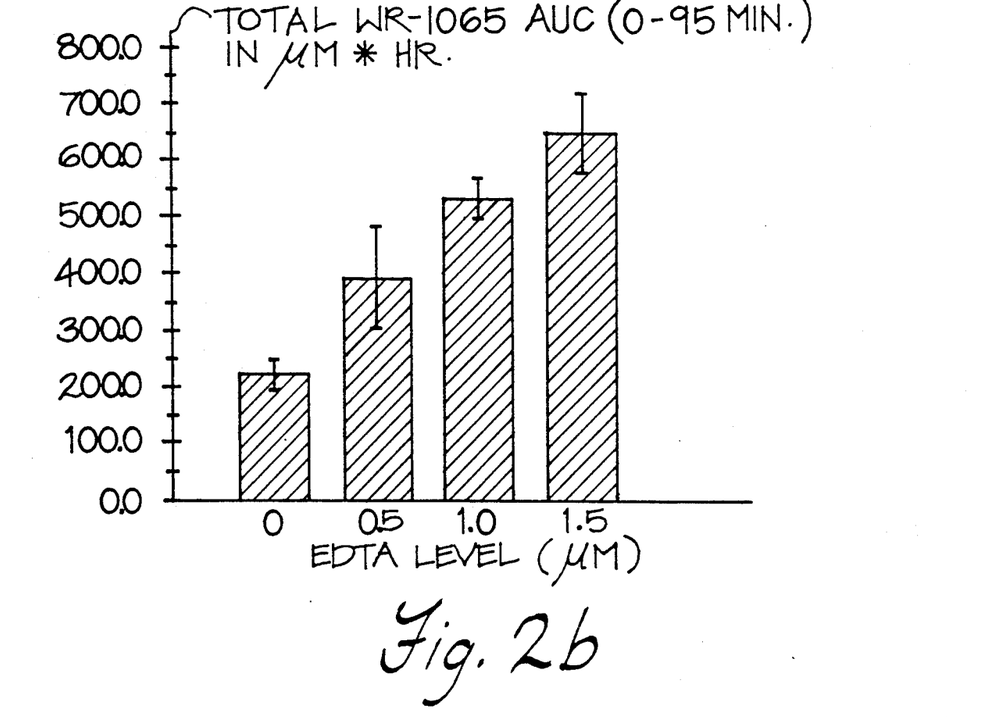
Figure 3:
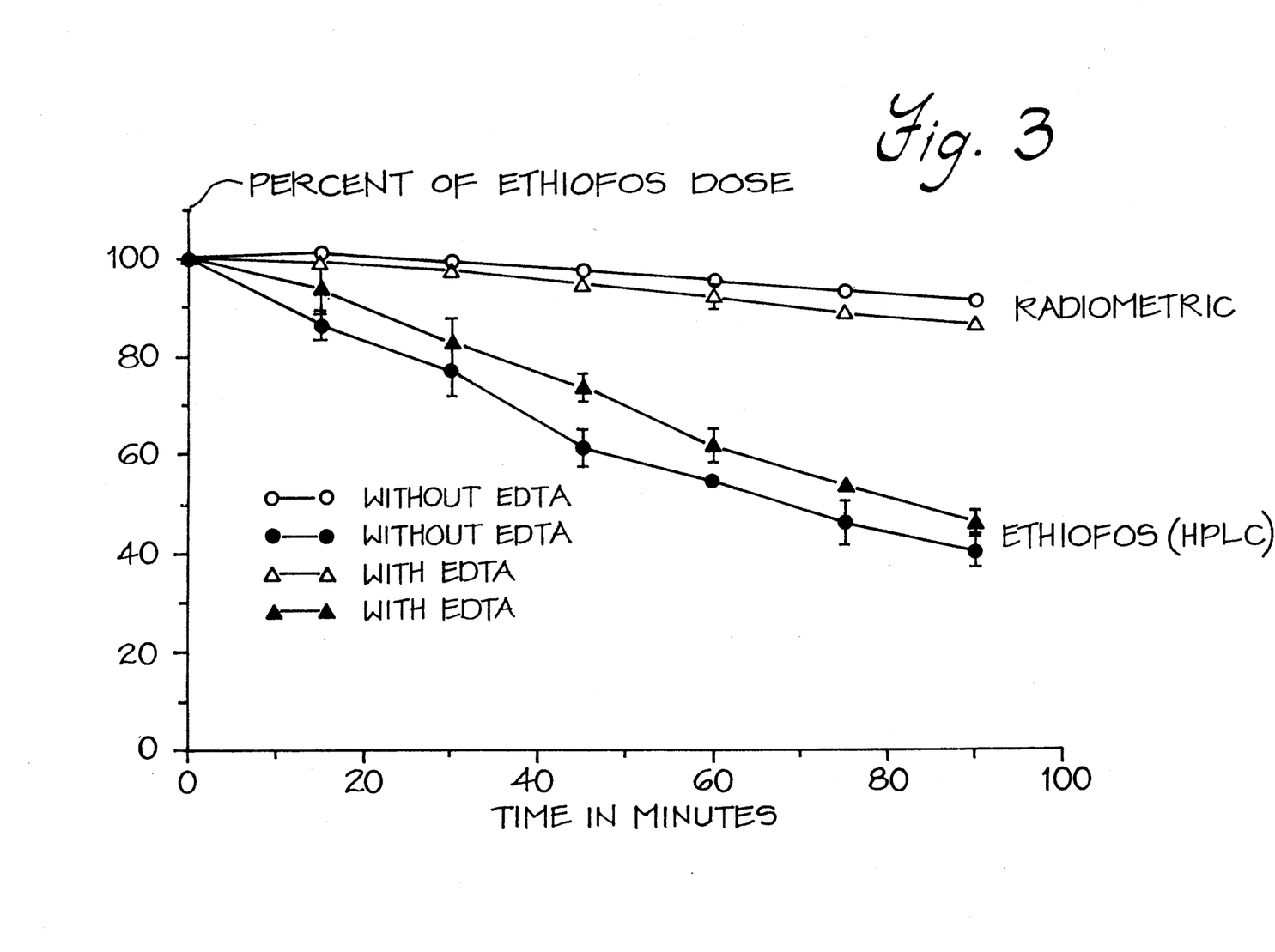
FIG. 3 demonstrates the disappearance of radioactive compound and ethiofos in the circulating intestinal perfusate.

FIG. 2 demonstrated the increase in plasma concentration of ethiofos with increasing dosage of EDTA. After 90 minutes of intestinal perfusion of radiolabelled ethiofos as described in Example 1A, 90.5±1.7% of the labelled ethiofos remained in the circulating perfusate. However, upon addition of disodiumethylenediaminetetraacetic acid (Na$_2$EDTA) at a 1.0 mM concentration, only 85.8±1.09% of the radioactivity remained in the perfusate. This decrease in perfusate ethiofos was accompanied by a significant increase in plasma concentration of both ethiofos and its metabolite WR-1065, as shown in FIGS. 1a and 2b, respectively. The increased radioprotection absorption was dose dependent, reaching a maximum at a concentration of approximately 1 mM EDTA. After 90 min of intestinal perfusion, 90.5±1.74% of the radioactivity remained in the circulating, ph-adjusted water solution. Treatment with 1 mM Na$_2$ EDTA in the same water solution indicated that 85.8±1.09% of the radioactivity remained after 90 min. This apparent small increase in absorption rate was corroborated by significant increases in both ethiofos and total WR-1065 levels in portal blood samples. FIG. 3 illustrates the disappearance profiles for the radioactivity and the intact parent compound for both treatments in the circulation intestinal perfusate.

Figure 4:
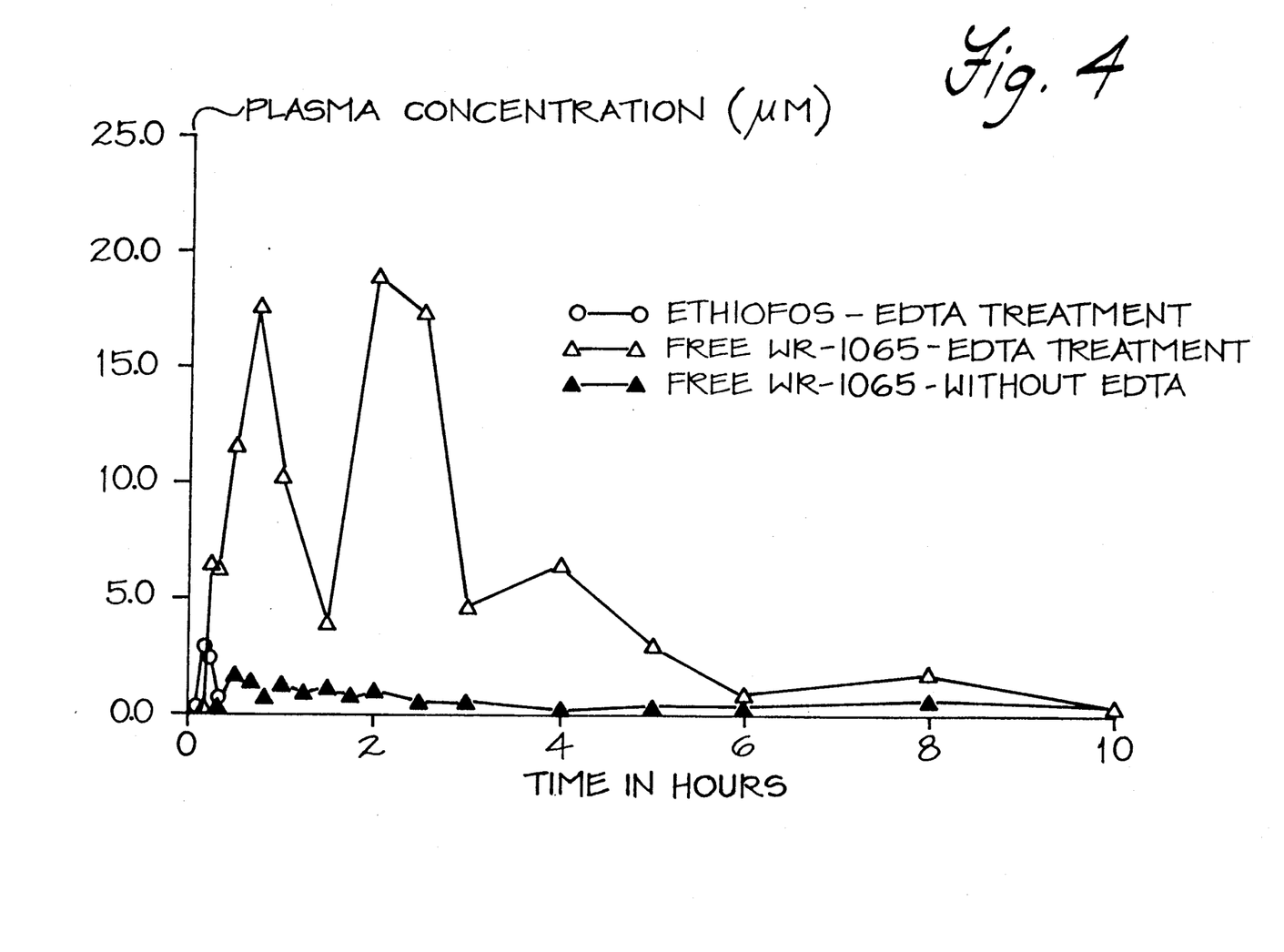
FIG. 4 demonstrates the EDTA enhanced absorption of ethiofos and WR-1065 in Rhesus monkey.

Similar results were obtained following intraduodenal administration of ethiofos to Rhesus monkeys. EDTA enhanced the absorption of ethiofos and WR-1065 in the Rhesus monkey, as demonstrated in FIG. 4. The area under the plasma concentration-time curve (AUC) for ethiofos was 0.55 mM:hr and 0 mM.hr in the presence and absence of 47:1 ratio of ethiofos to EDTA, respectively. WR-1065 AUC was 52.1 mM/hr and 6.6 mM/hr in the presence and absence of 47M concentration of EDTA, respectively. AUC is the expression of the amount of drug that accumulated in the blood over the time period monitored.

EXAMPLE 6

Comparison of Ethiofos Absorption Enhancers

Figure 5:
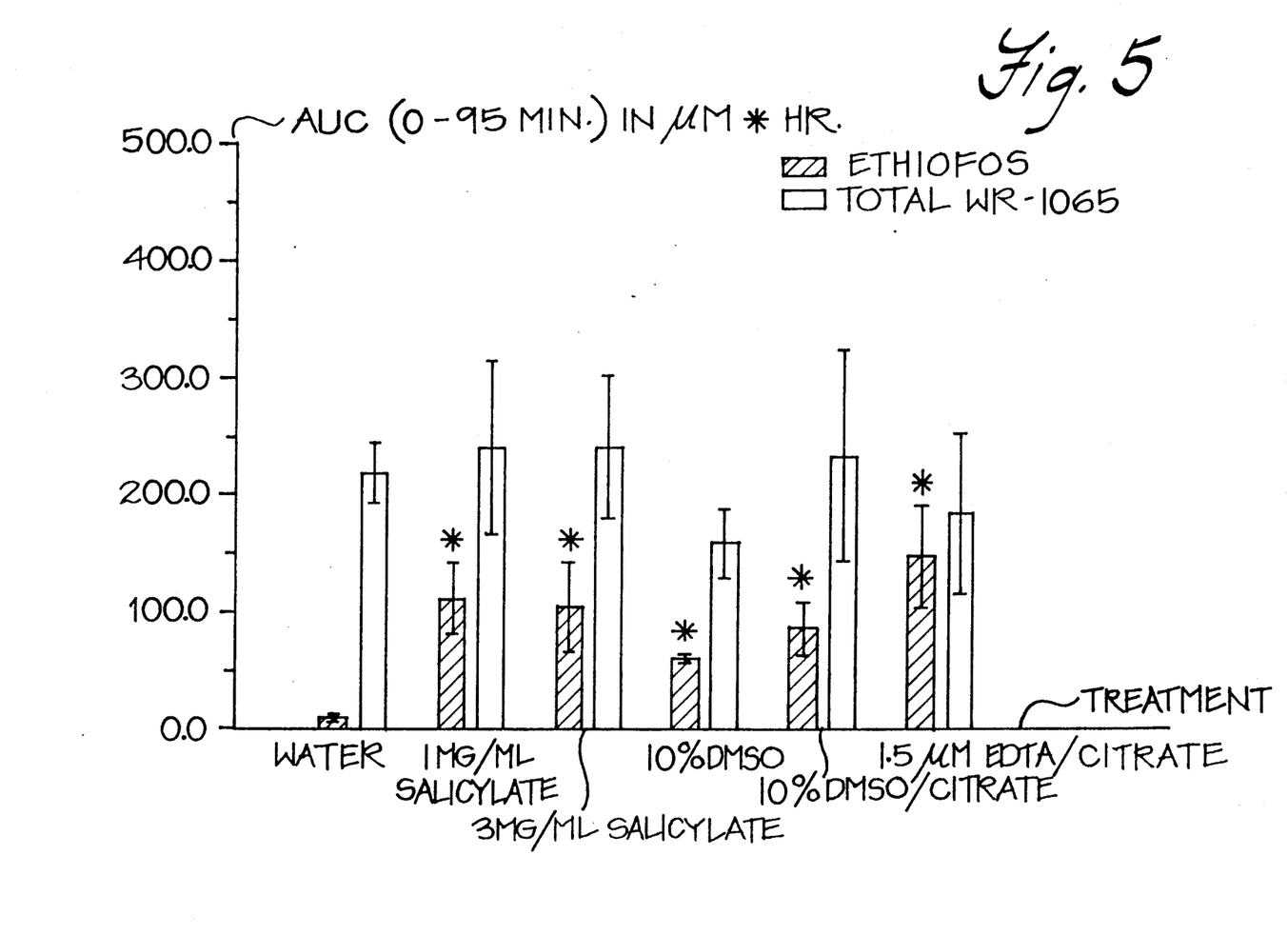
FIGS. 5 and 6 demonstrate the effect of various absorption enhancers and alkaline phosphatase inhibitors on ethiofos and total WR-1065 in rat portal blood.
Figure 6:
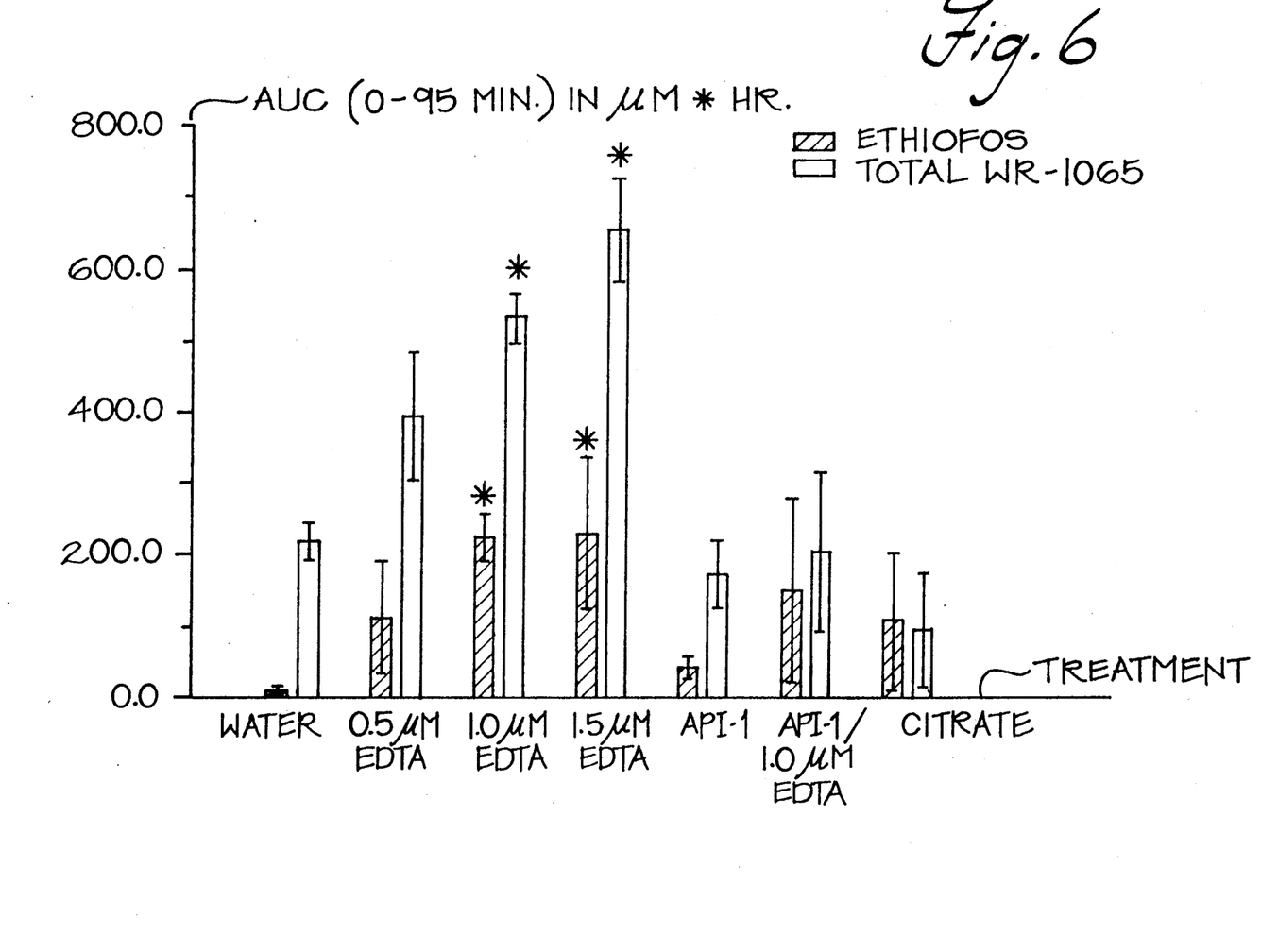

FIGS. 6 and 6 illustrate the effect of various absorption enhancers and alkaline phosphatase inhibitors on ethiofos and total WR-1065 concentrations in rat portal blood during the 90 minutes of in situ intestinal perfusion. The absorption enhancement observed for ethiofos by EDTA resulted in dose-related enhancements. Highest levels were achieved following a treatment of 1.5 mM EDTA. The appearance of ethiofos in the rat portal blood was increased by a factor of 20.

EXAMPLE 7

Ethiofos Absorption Enhancement by EDTA in Rat & Monkey Models

The rat in situ data demonstrated that EDTA provided some protection of ethiofos degradation in the lumen as well as increase the rate of absorption. In the Rhesus monkey, EDTA enhanced the absorption of ethiofos administered intraduodenally to the awake monkey. Coadministration of ethiofos with EDTA resulted in detectable levels of ethiofos and a substantial increase in the observed free and total WR-1065 levels in Rhesus monkey plasma. These data provide evidence that EDTA enhances absorption of the hydrophilic species (ethiofos and WR-1065) independent of methods (in situ versus in vivo) and species studied.

The drug forms of this invention are suitably administered in oral dosage form, such as by tablet or capsule, by combining the polar bioactive agent in a therapeutic amount and the hydroxyaryl or hydroxyaralkyl acid or salt ester or amide thereof in a sufficient quantity to be effective to enhance oral delivery with an oral pharmaceutically acceptable inert carrier, such as lactose, starch (pharmaceutical grade), dicalcium phosphate, calcium sulfate, Kaolin, mannitol and powdered sugar. In order to reduce the irritation in the stomach, the preferred dose form of the hydroxyaryl or hydroxyaralkyl acid should be a pharmaceutically acceptable salt and the drug form should be designed to release the polar bioactive agent and the hydroxyaryl or hydroxyaralkyl acid salt beyond the pylorus. In addition, when required, suitable binders, lubricants, disintegrating agents, and coloring agents can also be added. Typical binders include, without limitation, starch, gelatin, sugars such as sucrose, molasses, and lactose, natural and synthetic gums, such as acacia, sodium alginate, extract of Irish moss, carboxymethylcellulose, ethylcellulose, and polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose and wood products, alginic acid, guargum, citris pulp, carboxymethylcellulose, and sodium lauryl sulfate. Optionally, if desired, a conventionally, pharmaceutically acceptable dye can be incorporated into oral dosage unit form, e.g., any of the standard FD & C dyes.

Any skilled artisan concerned with the subject matter of this invention can prepare these oral dosage forms by simply referring to the oral dosage forms preparatory procedure outlined in REMINGTON'S PHARMACEUTICAL SCIENCES, Fifteenth Edision (1975), pages 1576 through 1617 inclusive.

From the foregoing description, one of ordinary skill in the art can easily ascertain the essential characteristics of this invention, and without departing from the spirit and scope thereof, can make various changes and modifications of the invention to adapt it to various usages and conditions. As such, such changes and modifications are properly, equitably, and intended to be, within the full range of equivalence of the following claims.

What is claimed:

1. A pharmaceutical composition for enhancing gastrointestinal tract absorption of a radioprotective drug comprising a therapeutically effective dosage amount of an orally or rectally administered ethiofos, and pharmaceutically acceptable salts thereof and a chelating agent selected from the group consisting of EDTA, EGTA, citrate and therapeutically acceptable salts thereof.

2. A method for enhancing the rate of gastrointestinal absorption of orally or rectally administered radioprotective agents comprising administration of a therapeutically effective dosage amount of the composition of claim 1.

3. An orally administered drug form comprising ethiofos and an absorption enhancer selected from the group consisting of EDTA and EGTA and therapeutically acceptable salts thereof.

4. The drug form of claim 3 wherein said drug form comprises microspheres encapsulating the ethiofos, the absorbtion enhancer or both.

5. The drug form of claim 4 further comprising microspheres encapsulating the EDTA without the ethiofos.

6. A method for radioprotection of an individual comprising administration of a therapeutically effective dosage of the composition of each of claims 1, 3, 4 and 5.

7. A pharmaceutical composition for enhancing gastrointestinal tract absorption of a polar compound comprising a therapeutically effective dosage amount of an orally or rectally administered ethiofos and a chelating agent selected from the group consisting of EDTA, EGTA, citrate and therapeutically acceptable salts thereof.

8. A pharmaceutical composition for enhancing absorption of a polar compound comprising a therapeutically effective dosage amount of an orally or rectally administered ethiofos and a chelating agent selected from the group consisting of EDTA, EGTA, citrate and therapeutically acceptable salts thereof.

9. A method for enhancing the rate of gastrointestinal absorption of orally or rectally administered ethiofos comprising administration of a therapeutically effective dosage amount of the composition of claim 8.

10. The orally administered drug of claim 7 in which a therapeutically acceptable salt is $Na_2$ EDTA.

* * * * *